United States Patent
Ye et al.

(10) Patent No.: US 10,024,778 B2
(45) Date of Patent: Jul. 17, 2018

(54) BACKSCATTERING SPECTROMETRY FOR DETERMINING A CONCENTRATION OF SOLIDS IN A SOLIDS-LADEN FLUID

(71) Applicant: Halliburton Energy Services, Inc., Houston, TX (US)

(72) Inventors: Xiangnan Ye, Cypress, TX (US); Dale E. Jamison, Humble, TX (US); Cato Russell McDaniel, The Woodlands, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 275 days.

(21) Appl. No.: 14/889,383

(22) PCT Filed: Nov. 24, 2014

(86) PCT No.: PCT/US2014/067096
§ 371 (c)(1),
(2) Date: Nov. 5, 2015

(87) PCT Pub. No.: WO2016/085447
PCT Pub. Date: Jun. 2, 2016

(65) Prior Publication Data
US 2016/0356692 A1 Dec. 8, 2016

(51) Int. Cl.
*G01N 21/00* (2006.01)
*G01N 15/06* (2006.01)
(Continued)

(52) U.S. Cl.
CPC ........... *G01N 15/06* (2013.01); *E21B 47/102* (2013.01); *E21B 47/1015* (2013.01);
(Continued)

(58) Field of Classification Search
CPC ........ G01N 15/06; G01N 15/14; G01N 21/49; G01N 2021/4709; G01N 2015/0846; G01V 3/30; E21B 49/00
See application file for complete search history.

(56) References Cited

U.S. PATENT DOCUMENTS 3,787,122 A    1/1974  Lepper, Jr.
5,159,569 A *  10/1992 Xu ....................... E21B 47/065
                                                    374/136
(Continued)

FOREIGN PATENT DOCUMENTS

CA          2731655 A1      2/2010
WO          9820321 A1      5/1998
WO     WO-2014042642 A1     3/2014

OTHER PUBLICATIONS

Fann Instrument Company, Dynamic HPHT® Filtration System, Model 90 Instruction Manual,2013.*
(Continued)

*Primary Examiner* — Shawn Decenzo
*Assistant Examiner* — Maurice Smith
(74) *Attorney, Agent, or Firm* — McDermott Will & Emery LLP (57) ABSTRACT

An apparatus including an electromagnetic radiation source that emits electromagnetic radiation, a sample chamber comprising a fluid sample inlet for introducing a solids-laden fluid sample therein, and a detector that receives a backscattering signal and generates an output signal corresponding to a concentration of solids in the solids-laden fluid sample. The electromagnetic radiation transmits through the sample chamber and optically interacts with the solids-laden fluid sample to generate a backscattering signal. The sample chamber may include one or more of a shear bob for applying a shear rate to the solids-laden fluid sample, the shear bob suspended in the sample chamber and rotatable
(Continued)

about an axis, a sealable fluid pressurizing inlet for pressurizing the sample chamber and a pressure gauge for measuring the pressure in the sample chamber when pressurized, and/or a temperature source for heating the solids-laden fluid sample.

15 Claims, 2 Drawing Sheets

(51) Int. Cl.
    *E21B 47/10*       (2012.01)
    *G01N 21/49*       (2006.01)
    *G01N 23/203*     (2006.01)
    *E21B 49/08*       (2006.01)
    *G01N 15/14*       (2006.01)
    G01N 21/47       (2006.01)
    *E21B 43/26*       (2006.01)
    G01V 3/30        (2006.01)

(52) U.S. Cl.
    CPC ....... E21B 49/081 (2013.01); G01N 15/1404 (2013.01); G01N 21/49 (2013.01); G01N 23/203 (2013.01); *E21B 43/26* (2013.01); *G01N 2015/0693* (2013.01); *G01N 2021/4709* (2013.01); *G01V 3/30* (2013.01)

(56) References Cited

U.S. PATENT DOCUMENTS

| | | | | |
|---|---|---|---|---|
| 5,801,820 | A * | 9/1998 | Bysouth | ............... G01N 35/085 356/36 |
| 6,055,874 | A * | 5/2000 | Onan | ...................... E21B 49/00 73/865.6 |
| 7,812,318 | B1 | 10/2010 | Auld | |
| 2005/0225760 | A1 | 10/2005 | Vijayakumar et al. | |
| 2007/0066877 | A1 | 3/2007 | Arnold et al. | |
| 2008/0066962 | A1 | 3/2008 | Rolovic et al. | |
| 2014/0202848 | A1* | 7/2014 | Kawanami | ............. H01L 51/56 204/192.17 |

OTHER PUBLICATIONS

Gustav Mie and the Scattering and Absorption of Light by Particles: Historic Developments and Basics, Journal of Quantitative Spectroscopy & Radiative Transfer 110: 787-799 (2009).

International Search Report and Written Opinion for PCT/US2014/067096 dated Aug. 19, 2015.

Australian Examination Report from Australian Patent Application No. 2014412768, dated Dec. 14, 2017, 4 pages.

* cited by examiner

BACKSCATTERING SPECTROMETRY FOR DETERMINING A CONCENTRATION OF SOLIDS IN A SOLIDS-LADEN FLUID

BACKGROUND

The exemplary embodiments herein relate generally to solids-laden fluids for use in subterranean formation operations and, more particularly, to determining the concentration of solids in solids-laden fluids for use in subterranean formation operations using backscattering spectrometry.

Hydrocarbon-producing wells, be they vertical, deviated, or horizontal wells, are generally drilled using a drilling fluid pumped down a drill string and through a drill bit attached to the end of the drill string. The drilling fluid serves, among other things, to lubricate and cool the cutting surfaces of the drill bit, transport drill cuttings to the surface, control formation pressure, and maintain well stability. Various particulates may be included in a drilling fluid to influence the effectiveness of the fluid or remediate or protect the subterranean formation, such as weighting agents (e.g., barite), lubricating agents, viscosifying agents, fluid loss agents, and the like.

Once a well is in place, stimulation of the well may be achieved using hydraulic fracturing treatments. In hydraulic fracturing treatments, a viscous treatment fluid may be pumped into a portion of a subterranean formation at a rate and pressure such that the subterranean formation breaks down and one or more fractures are formed. Typically, particulate solids, such as graded sand, are introduced into the subterranean formation in a portion of the treatment fluid and deposited into the fracture. These particulate solids (generally known as "proppant particulates" or, simply, "proppant") serve to prop the fracture open (e.g., keep the fracture from fully closing) after the hydraulic pressure is removed. By keeping the fracture from fully closing, the proppants aid in forming conductive paths through which fluids, such as hydrocarbons, may flow. Like with drilling fluids, other particulate additives may also be included in the treatment fluid to influence the effectiveness. Various particulates may be included in a drilling fluid to influence the effectiveness of the fluid or remediate or protect the subterranean formation, such as those mentioned with reference to drilling fluids, as well as other particulates such as gravel for forming a gravel pack.

The drilling fluids and treatment fluids comprising the particulate additives may be collectively referred to herein as solids-laden fluids. Such solids-laden fluids may experience a reduced solids carrying capacity, or sag, while in use in a subterranean formation or through equipment for use in performing a particular subterranean formation operation. As used herein, the term "sag" and all grammatical variants thereof refers to settling of particulate in a solids-laden fluid, including both static and dynamic conditions. The viscoelastic properties of the solids-laden fluids, exposure to shear, exposure to elevated shear rates, the geometric configuration of a wellbore (e.g., vertical or deviated), and the like, may have a significant effect on sag.

Sag may result in ineffective distribution of solids additives in the solids-laden fluid. Sag may cause the solids (e.g., weighting agents such as barite) to settle in a static or circulating solids-laden fluid in a wellbore, which may cause the upper portion of the wellbore to lose mud density, which may lessen the hydrostatic pressure and result in an influx of formation fluid. Sag may further result in failure of the solids-laden fluid to perform a particular function (e.g., failure of a fluid loss agent to reach a zone of interest or be evenly distributed in a wellbore), stuck pipe, or, in extreme cases, abandonment of a wellbore.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The embodiments herein relate generally to solids-laden fluids for use in subterranean formation operations and, more particularly, to determining the concentration of solids in solids-laden fluids for use in subterranean formation operations using backscattering spectrometry.

The embodiments herein include backscattering spectrometry apparatuses and methods of use of the apparatuses that are capable of determining the concentration of solids in a solids-laden fluid. Specifically, the backscattering spectrometry apparatuses and methods of use of the apparatuses herein may be used to simulate subterranean formation conditions to determine the concentration of solids in a solids-laden fluid to determine whether sag as a function of time has occurred in the fluid. Accordingly, the embodiments herein permit a solids-laden fluid to be tested, reformulated, and optimized based on known conditions or likely conditions that the solids-laden fluid will experience during a particular subterranean formation operation including, but not limited to, shearing conditions, pressure conditions, temperature conditions, and any combination thereof. The embodiments herein further allow real-time gathering of such information to determine whether a particular solids-laden fluid may begin to experience sag and to what extent.

Although some embodiments described herein are illustrated by reference to subterranean formation operations, the backscattering spectrometry apparatuses and methods disclosed herein may be used in any non-subterranean formation operation that may benefit from determining a concentration of solids in a solids-laden fluid under varying conditions. Such operations may be related to any industry including, but not limited to, oil and gas, mining, chemical, pulp and paper, aerospace, automotive, asphalt and/or concrete (e.g., portable paving applications), the pharmaceutical industry, the food industry, and the like.

Unless otherwise indicated, all numbers expressing quantities of ingredients, properties such as angled components, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the features disclosed herein are presented herein. Not all features of a physical implementation are described or shown in this application for the sake of clarity. It is understood that in the development of a physical embodiment incorporating the embodiments of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

The embodiments herein include a backscattering spectrometry apparatus (which may be referred to herein simply as "apparatus") according to one or more embodiments of the present disclosure. The apparatus uses backscattering to quantitatively determine a concentration of solids in a solids-laden fluid. The apparatus may simulate downhole conditions, such as shear, temperature, and/or pressure, allowing the apparatus to be used to quantitatively determine the effects of sag in particular solids-laden fluid formulations by evaluating a change in concentration of the solids-laden fluid over time. As used herein, the term "backscattering" generally refers to the reflection of electromagnetic radiation back in the general direction from which they came. As used herein, the term "electromagnetic radiation" refers to infrared and near-infrared radiation, visible light, ultraviolet light, X-ray radiation, gamma ray radiation, and combinations thereof. Backscattering is typically characterized by diffuse reflection, meaning that the incident ray is reflected at many angles rather than at just one angle as in the case of specular reflection.

Mie theory is a known scattering mathematical model that may be used to determine concentrations of essentially spherical particulates of varying sizes in a fluid. Solids used in solids-laden fluids for use in subterranean formation operations are typically spherical in shape and are specifically applicable to the Mie theory, although other solids that are substantially spherical may also be evaluated using the theory. Accordingly, as used herein, the term "solids" referring to the particulates in a solids-laden fluid refers to spherical and substantially spherical particulates. As used herein, the term "substantially" means largely but not necessarily wholly. According to Mie theory, backscattering of electromagnetic radiation is inversely proportional to the concentration of solids in a solids-laden fluid. Thus, electromagnetic radiation may be reflected from a solids-laden fluid and the backscattering detected, wherein Mie theory is applied to determine a value inversely proportional to the concentration of the solids in the solids-laden fluid and, therefore, the sag of the solids-laden fluid.

Figure 1:
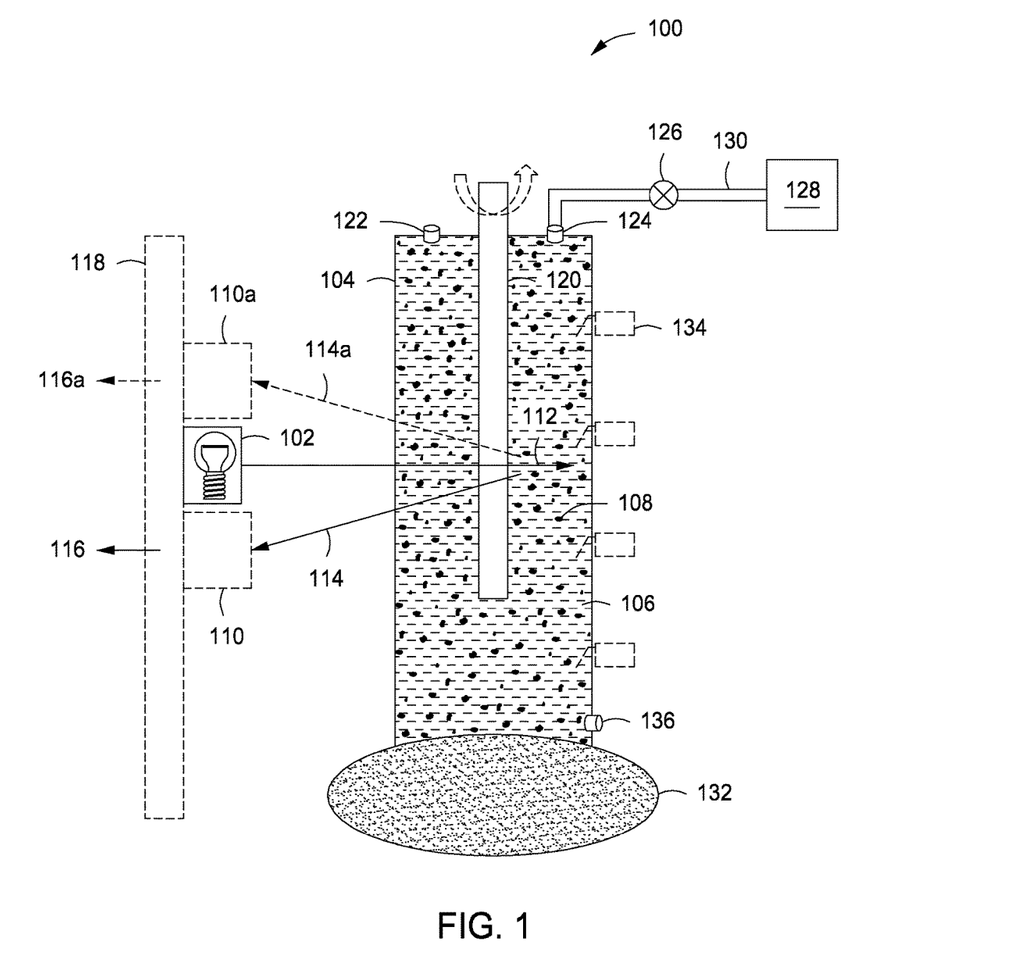
FIG. 1 depicts a backscattering spectrometry apparatus for determining the concentration of solids in a solids-laden fluid according to one or more embodiments of the present disclosure.

Referring now to FIG. 1, illustrated is a backscattering spectrometry apparatus 100 according to one or more embodiments of the present disclosure. As shown, apparatus 100 includes an electromagnetic source is 102, a sealable sample chamber 102 for housing a solids-laden fluid 106 having solids 108 therein, and a detector 110. The electromagnetic radiation source 100 emits electromagnetic radiation 112 that optically interacts with the solids-laden fluid 106 and generates a backscattering signal 114. As used herein, the term "optically interact," and grammatical variants thereof, refer to transmission, reflection, or scattering of electromagnetic radiation, wherein by virtue of the optical interaction, a change in the electromagnetic radiation occurs. Accordingly, optically interacted electromagnetic radiation refers to electromagnetic radiation that has been transmitted, reflected, or scattered with an electromagnetic radiation source, as well as by interaction with a solids-laden fluid or solids therein. The backscattering signal 114 may be received by the detector 110, wherein the detector generates an output signal 116 corresponding to a concentration of solids in the solids-laden fluid.

The electromagnetic radiation source 102 of the apparatus 100 may be positioned along an optical path to ensure optical interaction with the solids-laden fluid 106 in the sample chamber 104. Accordingly, the electromagnetic radiation source 102 may be positioned at any location along a height or width of the sample chamber 104. As depicted, the electromagnetic radiation source 102 is positioned at a location to the side of the sample chamber 104 along a height thereof; however, the electromagnetic radiation source 102 may be located at any position relative to the sample chamber 104 that permits the electromagnetic radiation to optically interact with the solids-laden fluid including, but not limited to, any side, the top, or the bottom of the sample chamber, without departing from the scope of the present disclosure. For example, the configuration of the sample chamber 104 may be horizontal or deviated (e.g., angled), rather than vertical as shown, and the electromagnetic radiation source 100 may be positioned at a location along the width (e.g., top portion) of the sample chamber 104.

In some embodiments, it may be desirable to optically interact electromagnetic radiation with the solids-laden fluid 106 at a variety of locations along the height or width of the sample chamber 104. In such embodiments, the electromagnetic radiation source 102 may be mounted on a slidable member 118 (shown in phantom). The slidable member 118 may be configured such that the electromagnetic radiation source 102 is stationary on the slidable member 118 and the slidable member 118 moves up or down to position the electromagnetic source at one or more locations along the height (as shown) or width (not shown) of the sample chamber 104. In other embodiments, the slidable member 118 may be configured such that the electromagnetic radiation source 102 is mounted thereon and is itself moveable relative to the slidable member 118, thereby permitting the electromagnetic radiation source 102 to be moved up or down to position the electromagnetic source 102 at one or more locations along the height (as shown) or width (not shown) of the sample chamber 104. The ability of apparatus 100 to permit electromagnetic radiation to optically interact with the solids-laden fluid 106 at a variety of locations may permit an operator to determine the concentration of solids at various positions in the solids-laden fluid 106, thereby permitting a gradient analysis of sag for a particular solids-laden fluid 106.

The electromagnetic radiation source 102, as discussed previously, may be configured to emit or otherwise generate electromagnetic radiation 112. The electromagnetic radiation source 102 may be any device capable of emitting or generating electromagnetic radiation, as defined herein. For example, the electromagnetic radiation source 102 may be a light bulb, a light emitting device (LED), a laser, a blackbody, a photonic crystal, an X-Ray source, a gamma ray source, combinations thereof, and the like. The electromagnetic radiation 112 emitted from the electromagnetic radiation source 102 for use in the apparatus 100 of the embodiments herein may include, but may not be limited to, infrared radiation, near-infrared radiation, visible light, ultraviolet light, X-ray radiation, gamma ray radiation, and any combination thereof.

The sample chamber 104 may generally be a sealable container having a volume capable of holding the solids-laden fluid 106. Although the sample chamber 104 is depicted as a rectangular prism, any shape capable of holding a solids-laden fluid 106 and allowing electronic radiation to interact therewith to produce a backscattering signal may be suitable for the apparatus 100 of the present disclosure. Generally, the shape of the sample chamber 104 is preferably such that the sample chamber 104 has a base that can balance the sample chamber 104 while having a solids-laden fluid 106 therein and/or while the apparatus 100 is in operation. It may also be preferred that the shape of the sample chamber 104 be symmetrical about two axis; such shapes may include, but are not limited to, a cube, a cuboid, a cylinder, a hexagonal prism, a triangular prism, and the like. However, bilateral symmetrical shapes may also be used for forming the sample chamber 104 without departing from the scope of the present disclosure including, but not limited to, a cone, a square-based pyramid, a rectangle-based pyramid, a triangular-based pyramid, and the like.

The size of the sample chamber 104 may be any size capable of holding a detectable volume of a solids-laden fluid 106 for determining a concentration of solids 108 therein, provided that a volume of space is permitted to evaluate sag. In some embodiments, the volume of the sample chamber 104 may be in the range of a lower limit of about 20 milliliters (mL), 50 mL, 100 mL, 150 mL, 200 mL, 250 mL, 300 mL, 350 mL, 400 mL, 450 mL, 500 mL, 550 mL, 600 mL, 650 mL, 700 mL, 750 mL, 800 mL, 850 mL, 900 mL, 950 mL, and 1000 mL to an upper limit of about 2000 mL, 1950 mL, 1900 mL, 1850 mL, 1800 mL, 1750 mL, 1700 mL, 1650 mL, 1600 mL, 1550 mL, 1500 mL, 1450 mL, 1400 mL, 1350 mL, 1300 mL, 1250 mL, 1200 mL, 1150 mL, 1100 mL, 1050 mL, and 1000 mL, encompassing any value and subset therebetween.

The material forming the sample chamber 104 of the apparatus 100 of the present disclosure may be a material that allows transmission of electromagnetic radiation 112 therethrough for optical interaction with the solids-laden fluid 106. In preferred embodiments, the material forming the sample chamber 104 does not optically interact with the electromagnetic radiation 112 at all or only slightly, such that the backscattering signal 114 received by the detector 110 is only backscattered from the solids-laden fluid 106 and not from the material forming the sample chamber 104. The sample chamber 104 may be composed from a variety of transparent, rigid or semi-rigid materials including, but not limited to, glasses, plastics, semi-conductors, crystalline materials, polycrystalline materials, hot or cold-pressed powders, quartz, fused quartz, and the like, and any combination thereof. The selection of material may be dependent on the particular spectrum of electromagnetic radiation 112 for a particular application. Various sample chambers 104 of different materials may be exchangeable within an apparatus 100 to account for various electromagnetic radiation 112 spectra, without departing from the scope of the present disclosure.

As depicted in FIG. 1, the sample chamber 104 may have a fluid sample inlet 122 where the solids-laden fluid 106 may be input into the sample chamber 104. The fluid sample inlet 122 may be any configuration (e.g., shape, size, and the like) suitable for introducing the solids-laden fluid 106 into the sample chamber 104. For example, the fluid sample inlet 122 may be large enough to pour the solids-laden fluid 106 therethrough, it may be configured to receive a funnel, tube, or other device for transferring the solids-laden fluid 106 from a first container into the sample chamber 104 therethrough, it may be sealable, hermetically sealable (e.g., for pressurizing applications, as discussed below), and the like, without departing from the scope of the present disclosure.

Similarly, the sample chamber 104 may comprise a fluid sample outlet 136 for removing the solids-laden fluid 106 from the sample chamber 104. As depicted, the fluid sample outlet 136 may be located substantially at the base of the sample chamber 104, where the solids-laden fluid 106 may be removed therethrough by means of gravity and in which the fluid sample outlet 136 is sealable to ensure that the solids-laden fluid 106 remains in the sample chamber 104 during the duration of testing operations. However, the fluid sample outlet 136 may be located at any position on the sample chamber 104, provided that it does not interfere with the ability of the sample chamber 104 to maintain the solids-laden fluid 106 in the sample chamber 104, without departing from the scope of the present disclosure. In some embodiments, the solids-laden fluid 106 may be removed from the sample chamber, as stated above, by gravity, by suction, by pouring, or any combination thereof. In preferred embodiments, the fluid sample outlet 136 may be hermetically sealable, particularly when a pressurizing system (e.g., the sealable fluid pressurizing inlet 124, the pressure gauge 126, and the pressurizing source 128) are used to pressurize the sample chamber 104.

In some embodiments, the sample chamber 104 may further comprise a wiper (not shown) configured to clean the sample chamber 104 after a solids-laden fluid 106 is removed from the sample chamber 104 through the fluid sample outlet 136. The wiper may be a blade with squeegee capable of traversing the interior of the sample chamber 104. In some embodiments, the sample chamber 104 may be cleaned by including a wash-and-suction vacuum port in the sample chamber 104 through which a cleaning fluid may be introduced into the sample chamber 104 and removed therefrom using a vacuum through the wash- and suction vacuum port. In some embodiments, the fluid sample inlet 122, the sealable fluid pressurizing inlet 124, or the fluid sample outlet 136 may be used as a wash-and-suction vacuum outlet, without departing from the scope of the present disclosure. In other embodiments, the sample chamber 104 may be manually cleaned, such as with a fabric cloth.

With continued reference to FIG. 1, in some embodiments, the sample chamber 104 of the apparatus 100 of the present disclosure may further a shear bob 120 for applying a shear rate to the solids-laden fluid 106. Applying shear to a solids-laden fluid 106 may be to mimic the shear stresses or rates expected to be applied to the solids-laden fluid 106 in a subterranean formation (i.e., downhole) environment or during exposure to equipment (e.g., pumping equipment) during a subterranean formation operation, which may affect sag. By subjecting the solids-laden fluid to a shear rate variable, the concentration of the solids 108 at a particular location in the solids-laden fluid 106 may be determined and the solids-laden fluid 106 may be optimized to withstand the shear rate for actual use in a subterranean formation or in an associated subterranean formation operation. Accordingly, the shear rate applied to the solids-laden fluid 106 may be any shear rate that the fluid would be expected to experience in a subterranean formation or during a subterranean formation operation. In some embodiments, the shear rate applied to the solids-laden fluid 106 by the shear bob 120 is in the range of from a lower limit of about 1 reciprocal seconds ($s^{-1}$), 50 $s^{-1}$, 100 $s^{-1}$, 150 $s^{-1}$, 200 $s^{-1}$, 250 $s^{-1}$, 300 $s^{-1}$, 350 $s^{-1}$, 400 $s^{-1}$, 450 $s^{-1}$, and 500 $s^{-1}$ to an upper limit of about 1000 $s^{-1}$, 950 $s^{-1}$, 900 $s^{-1}$, 850 $s^{-1}$, 800 $s^{-1}$, 750 $s^{-1}$, 700 $s^{-1}$, 650 $s^{-1}$, 600 $s^{-1}$, 550 $s^{-1}$, and 500 $s^{-1}$, encompassing any value and subset therebetween.

The shear bob 120 may be suspended in the sample chamber 104 and rotatable about an axis, which may be a vertical axis or a deviated axis from the vertical. In some embodiments, the shear bob 120 may be rotatable about an axis deviated from the vertical by no more than about 90° C.; a horizontal axis is within the scope of the present disclosure. The shear bob 120 is preferably configured to rotate and achieve couette flow. As used herein, the term "couette flow" refers to the laminar flow of a viscous fluid in a space between two parallel planes, one of which is moving relative to the other. Achieving couette flow with the shear bob 120 in the sample chamber 104 described herein permits a shear rate to be applied to the solids-laden fluid 106 may be calculated and maintained as substantially constant. Typically, to achieve couette flow, the shear bob 120 may be in the shape of a concentric cylinder, although other shapes may be used if they achieve couette flow to maintain constant shear.

The shear bob 120, as depicted, extends outside of the interior of the sample chamber 104; however, it will be appreciated that any other configuration may be used in accordance with the embodiments of the present disclosure, such as maintaining the entirety of the shear bob 120 within the sample chamber 104. Additionally, the shear bob 120 need not extend from the top of the sample chamber 104, but may instead extend from the bottom or base of the sample chamber 104 and extend upward where it may or may not contact the top of the sample chamber 104. That is, the shear bob 120 may traverse the entire height of the sample chamber 104 or may only traverse a portion, without departing from the scope of the present disclosure.

As depicted, the shear bob 120 may take up a volumetric space of about ⅕ of the volume of the sample chamber 104. However, the shear bob 120 may be of other sizes, without departing from the scope of the present disclosure, provided that it is capable of achieving couette flow, as discussed previously. For example, in some embodiments, the shear bob 120 may take up a volume in the range of a lower limit of about 5%, 10%, 15%, 20%, 25%, 30%, 35%, and 40% to an upper limit of about 80%, 75%, 70%, 65%, 60%, 55%, and 50% of the volume of the sample chamber 104, encompassing any value and subset therebetween.

Like the sample chamber 104, the shear bob 120 may be preferably made of a material that does not interfere with the optical interaction of the electromagnetic radiation with the solids-laden fluid 106, so as to reduce any stray backscattered light that may be detected by the detector 110 and reduce the output signal 110 corresponding to the concentration of solids 108 in the solids-laden fluid 106. In some embodiments, the shear bob 120 may be composed from a variety of transparent, rigid or semi-rigid materials including, but not limited to, glasses, plastics, semi-conductors, crystalline materials, polycrystalline materials, hot or cold-pressed powders, quartz, fused quartz, and the like, and any combination thereof.

In some embodiments, the concentration of solids 108 in the solids-laden fluid 106 may be affected by pressure, such as pressures encountered in a downhole location, which may cause the solids 108 to settle. Accordingly, the solids-laden fluid 106 may be preferably evaluated and reformulated upon exposure to such pressures, which may be further in combination with the expected shear rate exposure, as discussed previously. Thus, with continued reference to FIG. 1, the sample chamber 104 may further comprise (with or without the shear bob 120) a sealable fluid pressurizing inlet 124. The sealable fluid pressurizing inlet 124 is preferably hermetically sealable such that air or other fluids cannot escape through the sealable fluid pressurizing inlet 124 and interfere with pressurization of the sample chamber 104. The sealable fluid pressurizing inlet 124 may be coupled to a pressure gauge 126 for measuring the pressure in the sample chamber 104 when it is pressurized. A pressurizing source 128 may be used to provide a pressurizing fluid (not shown) for pressurizing the sample chamber 104 through the sealable fluid pressurizing inlet 124. The sealable fluid pressurizing inlet 124, the pressure gauge 126, and the pressurizing source 128 may be hermetically connected, such as through a tubular 130 (e.g., a hose), to form a sealed pressurizing system for pressurizing the sample chamber 104. In some embodiments, the pressure gauge 126 may be directly in contact with sample chamber 104 of the pressurizing source 128, or, as shown, in line between the two, without departing from the scope of the present disclosure.

In some embodiments, the pressurizing source 128 may be an air compressor, a fluid sprayer, or a shower system that provides a pressurizing fluid into the sample chamber 104 to pressurize the sample chamber 104. The pressurizing source 128 preferably is able to maintain a substantially constant pressure within the sample chamber 128 over a period of time, the pressure selected by an operator based on a pressure condition the solids-laden fluid 106 therein is expected to encounter, such as in a subterranean formation. The pressurizing fluid source may provide any pressurizing fluid capable of pressurizing the sample chamber 104 including, but not limited to, an inert gas (e.g., air), a non-miscible fluid, and any combination thereof. Specific examples of pressurizing fluid may include, but are not limited to, water, crude oil, natural gas, and the like, and combinations thereof.

The sample chamber 104 may be pressurized to any pressure expected to be found in a subterranean formation and capable of being maintained by the sample chamber 104. In some embodiments, the sample chamber 104 may be pressurized to a pressure in the range of a lower limit of about 500 pounds per square inch (psi), 1000 psi, 1500 psi, 2000 psi, 2500 psi, 3000 psi, 3500 psi, 4000 psi, 4500 psi, and 5000 psi to an upper limit of about 10000 psi, 9500 psi, 9000 psi, 8500 psi, 8000 psi, 7500 psi, 7000 psi, 6500 psi, 6000 psi, 5500 psi, and 5000 psi, encompassing any value and subset therebetween.

In some embodiments, the sample chamber 104 may further comprise a temperature source 132 for heating the solids-laden fluid 106 in the sample chamber 104 to simulate the temperature experienced by a solids-laden fluid 106 in a subterranean formation, which may influence and, in some cases, substantially influence sag of the solids 108 in the solids-laden fluid 106. The temperature source 132 may form a portion of the apparatus 100 alone or in combination with one or more of the shear bob 120 and the sealable fluid pressurizing inlet 124, the pressure gauge 126, and the pressurizing source 128. That is, the apparatus 100 disclosed herein may be equipped to impart one or all of shear, pressure, and temperature variables to the solids-laden fluid 106 for determining a concentration of solids 108 therein and the subsequent susceptibility of sag under those conditions.

The heating source 132 may be any device or component capable of imparting heat to the solids-laden fluid 106. The heating source 132 may form an integral part of the sample chamber 132, the apparatus 100, or may be removable or external thereto. For example, as depicted, the thermal source 132 may be in the form of a heating element that may be located at the base of the sample chamber 104. However, it will be appreciated that other forms of heating sources 132 may additionally be employed provided that the heating source 104 is able maintain a substantially constant temperature, thus allowing the solids-laden fluid 106 to maintain a substantially constant temperature, without departing from the scope of the present disclosure. For example, in some embodiments, the heating source 132 may be in the form of a heat lamp located at any position relative to the sample chamber 104 (e.g., the top, side, or bottom portion of the sample chamber 104), a heat jacketing element, a heat coil, a heated non-miscible fluid bath (for the sample chamber 104 or the entire apparatus 100), and the like.

The heating source 132 may heat the solids-laden fluid 106 in the sample chamber 104 to a temperature simulating any temperature the solids-laden fluid 106 would be expected to encounter in a subterranean formation or during a subterranean formation operation, such that the apparatus 100 may be used to determine sag of the solids 108 therein. In some embodiments, the heating source 132 may heat the solids-laden fluid 106 to a temperature in the range of a lower limit of about 5° C., 15° C., 30° C., 45° C., 60° C., 75° C., 100° C., 115° C., 130° C., 145° C., and 160° C. to an upper limit of 300° C., 275° C., 260° C., 245° C., 230° C., 215° C., 200° C., 175° C., and 160° C., encompassing any value and subset therebetween.

When a heating source 132 is included in the apparatus 100, such as part of the sample chamber 104, one or more thermal conductivity probes 134 may be positioned at any location along a height or width of the sample chamber 104. The thermal conductivity probes 134 may be used to evaluate the thermal conductivity of the solids-laden fluid 106, preferably at various locations along the height or width of the sample chamber 104, representing various depths at which sag may take place. Thermal conductivity is the property of a material (e.g., the solids-laden fluid 106) to conduct heat. The thermal conductivity of a solids-laden fluid 106 may be dependent on the type and concentration of solids 106 therein, and at any particular depth therein. The thermal conductivity of a solids-laden fluid 106 is a linear function of solids content in solids-laden fluid, which can be used to monitor the sag over time.

As previously mentioned, the thermal conductivity probes 134 may be positioned at any location along the height or width of the sample chamber 104 for monitoring the thermal conductivity of the solids-laden fluid 106. In some embodiments, at least two thermal conductivity probes 134 are positioned along the height or width of the sample chamber 104, although greater than two, such as three, four (as shown), five, or more may be positioned therealong. In some embodiments, the entirety of a portion of the height or width of the sample chamber 134 may have thermal conductivity probes 134 positioned thereon. In some embodiments, when two or more thermal conductivity probes 134 are positioned along the height or width of the sample chamber 104, they may be evenly spaced or randomly spaced therealong, without departing from the scope of the present disclosure. The value of spacing the thermal conductivity probes 134 is that it allows an operator to evaluate the thermal conductivity, associated with the presence of low and high gravity solids 108, at various locations throughout the solids-laden fluid 106 column in the sample chamber 104, thereby better evaluating the sag properties of a particular solids-laden fluid 106.

The thermal conductivity probes 134 for use in the embodiments herein may be commercially available probes and may provide real-time or near real-time thermal conductivity readings. The probes may be sensor-type probes that adhere to the sample chamber 104 or may be needle probes that extend through the sample chamber 104 material and into the interior of the sample chamber 104 in which the solids-laden fluid 106 is contained. In such instances, the thermal conductivity probes 134 may be sealed such that the sample chamber 104 is able to maintain the solids-laden fluid 104 without leakage or, preferably hermetically sealed such that the sample chamber 104 may be pressurized.

In some embodiments, the thermal conductivity probes 134 may take thermal conductivity measurements based on transient techniques, typically during the process of heating with the heating source 132. Such transient techniques may include, but are not limited to, the transient plane source method, the modified transient plane source method, the transient line source method, the laser flash method, the 3ω-method, the time-domain thermoreflectance method, and any combination thereof. In other embodiments, however, the thermal conductivity measurements may be based on steady-state techniques, such as Searle's bar method, Lees' disc method, and combinations thereof, without departing from the scope of the present disclosure.

As previously discussed, and with continued reference to FIG. 1, the electromagnetic source 102 may emit electromagnetic radiation 112 into an optical path, transmit through the sample chamber 104 and optically interact with the solids-laden fluid 106 therein. The optically interacted electromagnetic radiation 112 generates a backscattering signal 114 that is detected by a detector 110. The detector may be any device capable of receiving the backscattering signal and generating an output signal 116 corresponding to a concentration of the solids 108 in the solids-laden fluid 106, such as at a particular depth relative to the sample chamber 104. In some embodiments, the detector may be an infrared radiation detector, a near-infrared radiation detector, a visible light detector, an ultraviolet light detector, an X-ray radiation detector, a gamma ray radiation detector, and any combination thereof. Specific examples of detectors may include, but are not limited to a photocell, a thermocouple, a bolometer, a photovoltaic cell, a photoemissive cell, a photoconductive cell, a scintillation detector, and the like, and any combination thereof. The detector 110 may be configured to generate an output signal 116 for analysis and quantification. For example, in some embodiments, the output signal 116 may be in the form of a photocurrent that is inversely proportional to the concentration of the solids 108 in the solids-laden fluid 106, and may be based on light intensity.

As depicted in FIG. 1, the detector 110 may be located below the electromagnetic radiation source 102 and, if desired may be mounted onto the slideable member 118, but need not be. However, the detector may be placed at any location relative to the sample chamber 104 and electromagnetic radiation source 102 such that it receives the backscattering signal, without departing from the scope of the present disclosure. For example, as shown in phantom, the detector 110a may be placed at a location above the electromagnetic radiation source 102 configured to receive backscattering signal 114a, which may generate an output signal 116a therefrom. Moreover, the location of the detector 110 relative to the electromagnetic radiation source is not determinative provided that the detector 110 is capable of receiving one or more backscattering signals 116. Further, in some embodiments, the detector 110 and the electromagnetic radiation source 102 may be integral in a single component, such that the electromagnetic source 102 emits electromagnetic radiation 112 and the detector 110 surrounds or is otherwise connected to the electromagnetic source 102. For example, an integral electromagnetic source 102 and detector 110 may be configured as substantially a cube, where the electromagnetic radiation source 102 emits electromagnetic radiation 112 from a central location in the cube and the detector 110 comprises a radial portion of the cube from the electromagnetic radiation source 102 outward to the edge of the cube. Other configurations may also be suitable without departing from the scope of the present disclosure, provided that the detector is capable of receiving the backscattering light 116.

In some applications, the output signal 116 may be conveyed to or otherwise received by a signal processor (not shown) communicably coupled to the detector 110. The signal processor may be a computer including a non-transitory machine-readable medium, and may be configured to provide the resulting output signal 116 corresponding to a concentration of the solids 108 in the solids-laden fluid 106. The resulting output signal 116 may be readable by an operator who can consider the results and make proper adjustments or take appropriate action, if needed. In some embodiments, the resulting signal output 116 may be conveyed, either wired or wirelessly, to an operator for consideration. In other embodiments, the resulting output signal 116 of the concentration of solids 108 in the solids-laden fluid 106 may be recognized by the signal processor as being within or without an acceptable limit range, as discussed below.

The backscattering spectrometry apparatus 100 of FIG. 1 can be used to assign a solids carrying capacity to a solids-laden fluid 106 based on the output signal 116 generated. In some embodiments, a series of output signals 116 may be used to determine a solids-laden carrying capacity, which is dependent on the composition of the solids-laden fluid 106 and the variables to which it was subjected with the apparatus 100 (e.g., temperature, pressure, shear), which may dependent upon the expected subterranean formation variables in will encounter during operational use. As used herein, the terms "solids carrying capacity" or "carrying capacity," and grammatical variants thereof, refer to an amount of solids that a particular fluid type can maintain in suspension over a given period of time, which may be dependent upon the duration of a subterranean formation operation, for example. Although a single output signal 116 may be used to determine the carrying capacity of a solids-laden fluid 106, a series of output signals 116 collected along a trajectory representing a depth column may be preferred in order to establish a gradient of sag over time. For example, a sample chamber 104 in the apparatus 100 may have a height of a lower limit of about 5 centimeters (cm), 10 cm, 15 cm, 20 cm, 25 cm, 30 cm, 35 cm, 40 cm, 45 cm, and 50 cm to an upper limit about 100 cm, 95 cm, 90 cm, 85 cm, 80 cm, 75 cm, 70 cm, 65 cm, 60 cm, 55 cm, and 50 cm, encompassing any value and subset therebetween, wherein the height represents a depth column, and an output signal collected along that depth column may be used, and output signals 116 at any location therealong may be collected for establishing a carrying capacity.

In some embodiments, a solids carrying capacity threshold may be assigned to a particular solids-laden fluid 106, which represents the threshold value of solids 108 concentration in a solids-laden fluid (which may also be at a location in a depth column) at which, if exceeded, the solids-laden fluid 106 is unsuitable or undesirable for use in a particular subterranean formation operation. That is, if the output signal 116 exceeds the solids carrying capacity assigned to a particular solids-laden fluid 106, it may have a sag quality that will adversely affect the subterranean formation operation or the productivity of a wellbore. Accordingly, in some embodiments, when a solids-laden fluid 106 produces an output signal 116 with the apparatus 100 described herein that exceeds the solids carrying capacity threshold, remedial measures may be undertaken including reformulating the solids-laden fluid 106 and retesting using the same parameters (e.g., shear, temperature, pressure, time) used previously in order to optimize the carrying capacity of the solids-laden fluid 106. The solids-laden fluid 106 may be reformulated by adjusting the type, concentration, or mixture of solids therein; the type, concentration, or mixture of other additives required or desired for use in a particular subterranean formation or operation (e.g., liquid additives for fluid loss, lubricants, solvents, emulsifiers, viscosifiers, surfactants, other solids, and the like); and combinations thereof.

In some embodiments, the shear bob 120 in the sample chamber 104 may be rotated to apply a shear rate to a solids-laden fluid 106 therein. The shear bob 120 may be rotated at the shear rate prior to transmitting the electromagnetic radiation 112 through the sample chamber 104 and optically interacting it with the solids-laden fluid 106. In some embodiments, the electromagnetic radiation 112 may optically interact over an incremental period of time to determine the effect of the shear rate on the sag, or carrying capacity, of the solids-laden fluid 106, or the electromagnetic radiation 112 may optically interact once or more than once after a prolonged waiting period with the solids-laden fluid 106 experiencing shear. Moreover, the shear rate applied by the shear bob 120 may be steady over time, increased over time, or decreased over time, without departing from the scope of the present disclosure. When shear is applied to a solids-laden fluid 106, the solids carrying capacity threshold of the solids-laden fluid 106 may be assigned based on the shear rate applied, thereby establishing a shear-solids carrying capacity threshold. If the output signal 116 exceeds the shear-solids carrying capacity threshold, the solids-laden fluid 106 may be reformulated, as described above.

In some instances, the sample chamber 104 may be pressurized in accordance with the embodiments described herein. The sample chamber 104 may be pressurized prior to transmitting the electromagnetic radiation 112 through the sample chamber 104 and optically interacting it with the solids-laden fluid 106. In some embodiments, the electromagnetic radiation 112 may optically interact over an incremental period of time to determine the effect of the pressurization on the sag, or carrying capacity, of the solids-laden fluid 106, or the electromagnetic radiation 112 may optically interact once or more than once after a prolonged waiting period with the solids-laden fluid 106 experiencing pressurization. Moreover, the pressure applied may be steady over time, increased over time, or decreased over time, without departing from the scope of the present disclosure. When pressure is applied to a solids-laden fluid 106, the solids carrying capacity threshold of the solids-laden fluid 106 may be assigned based on the pressure applied, thereby establishing a pressure-solids carrying capacity threshold. If the output signal 116 exceeds the pressurized-solids carrying capacity threshold, the solids-laden fluid 106 may be reformulated, as described above.

In yet other embodiments, the temperature source 132 may be used to heat a solids-laden fluid 106 in the sample chamber 104 of the apparatus 100. The temperature source 132 may heat the solids-laden fluid 106 prior to transmitting the electromagnetic radiation 112 through the sample chamber 104 and optically interacting it with the solids-laden fluid 106. In some embodiments, the electromagnetic radiation 112 may optically interact over an incremental period of time to determine the effect of the heat on the sag, or carrying capacity, of the solids-laden fluid 106, or the electromagnetic radiation 112 may optically interact once or more than once after a prolonged waiting period with the solids-laden fluid 106 experiencing heat. Moreover, the heat applied by the temperature source 132 may be steady over time, increased over time, or decreased over time, without departing from the scope of the present disclosure. When heat is applied to a solids-laden fluid 106, the solids carrying capacity threshold of the solids-laden fluid 106 may be assigned based on the heat applied, thereby establishing a heated-solids carrying capacity threshold. If the output signal 116 exceeds the heated-solids carrying capacity threshold, the solids-laden fluid 106 may be reformulated, as described above.

A combination of the shear, pressure, and temperature variables described above may be applied to a particular solids-laden fluid 106, without departing from the scope of the present disclosure. Indeed, the interplay between each of these factors is typically found in a subterranean formation environment, with each influencing the carrying of a particular solids-laden fluid 106. Such a solids-laden fluid 106 may be optimized by formulating a solids-laden fluid that does not exceed any one of the shear-solids carrying capacity under a particular shear rate, the pressurized-solids carrying capacity under a particular pressure, and the heated-solids carrying capacity under a particular temperature. In other embodiments, all three variables may be applied to the solids-laden fluid 106 simultaneously and a carrying capacity reflecting the parameters as a whole assigned and tested (e.g., a shear/pressurized/heated-solids carrying capacity), without departing from the scope of the present disclosure.

The ability to reformulate a solids-laden fluid 106 based on its carrying capacity is a major advantage of the present disclosure. Indeed, such reformulation may occur prior to ever introducing the solids-laden fluid 106 into a subterranean formation, thereby avoiding potential costly remedial measures or potential wellbore abandonment for use of solids-laden fluids 106 that are inferior or woefully inadequate.

Figure 2:
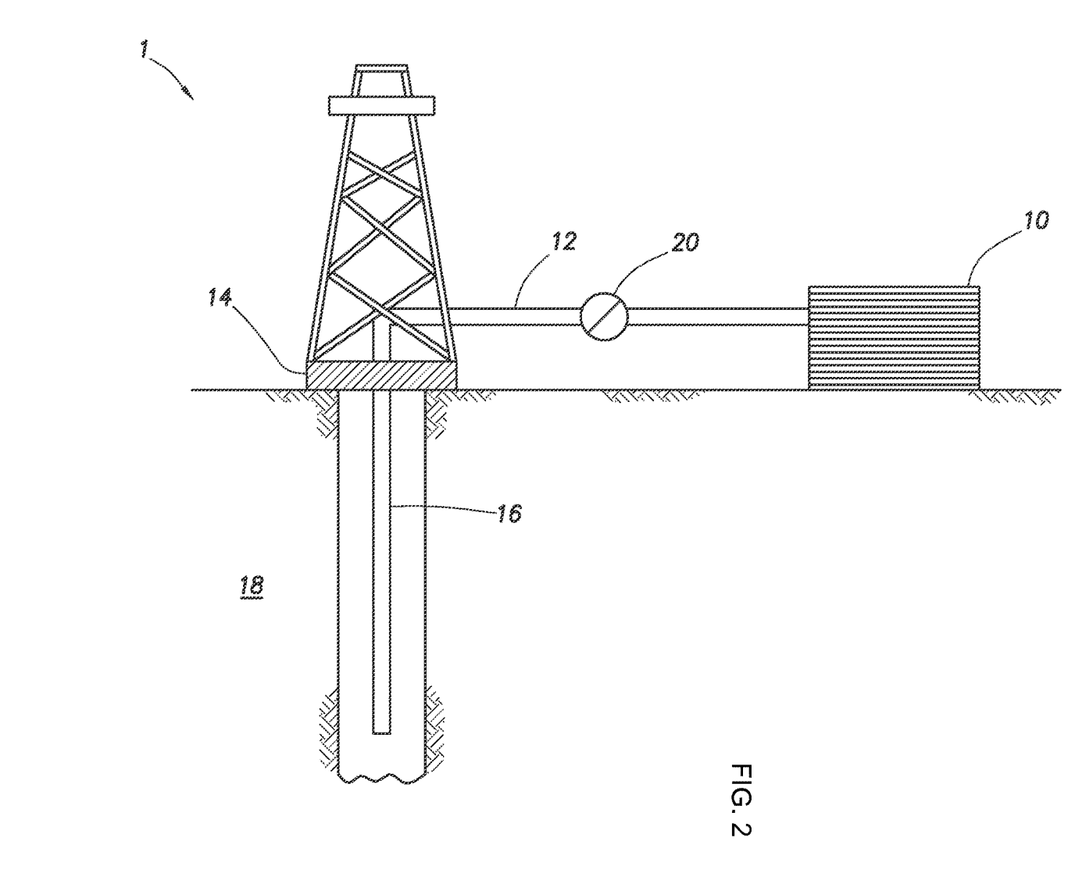
FIG. 2 depicts an embodiment of a system configured for delivering the solids-laden fluids of the embodiments described herein to a downhole location.

The reformulated solids-laden fluids of the embodiments described herein may be introduced into a subterranean formation by a number of mechanisms. FIG. 2 shows an illustrative schematic of a system that can deliver the reformulated solids-laden fluids (referred to below simply as "fluids") of the present disclosure to a downhole location, according to one or more embodiments. It should be noted that while FIG. 2 generally depicts a land-based system, it is to be recognized that like systems may be operated in subsea locations as well. As depicted in FIG. 2, system 1 may include mixing tank 10, in which the fluids of the embodiments herein may be formulated. The fluids may be conveyed via line 12 to wellhead 14, where the fluids enter tubular 16, tubular 16 extending from wellhead 14 into subterranean formation 18. Upon being ejected from tubular 16, the fluids may subsequently penetrate into subterranean formation 18. Pump 20 may be configured to raise the pressure of the fluids to a desired degree before introduction into tubular 16. It is to be recognized that system 1 is merely exemplary in nature and various additional components may be present that have not necessarily been depicted in FIG. 2 in the interest of clarity. Non-limiting additional components that may be present include, but are not limited to, supply hoppers, valves, condensers, adapters, joints, gauges, sensors, compressors, pressure controllers, pressure sensors, flow rate controllers, flow rate sensors, temperature sensors, and the like.

Although not depicted in FIG. 2, the fluid may, in some embodiments, flow back to wellhead 14 and exit subterranean formation 18. In some embodiments, the fluid that has flowed back to wellhead 14 may subsequently be recovered and recirculated to subterranean formation 18.

It is also to be recognized that the disclosed fluids may also directly or indirectly affect the various downhole equipment and tools that may come into contact with the fluids during operation. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the systems generally described above and depicted in FIG. 2.

Embodiments disclosed herein include Embodiment A, Embodiment B, and Embodiment C.

Embodiment A

An apparatus comprising: an electromagnetic radiation source that emits electromagnetic radiation; a sample chamber comprising a fluid sample inlet for introducing a solids-laden fluid sample therein, wherein the electromagnetic radiation transmits through the sample chamber and optically interacts with the solids-laden fluid sample to generate a backscattering signal, the sample chamber further comprising one or more of: a shear bob for applying a shear rate to the solids-laden fluid sample, the shear bob suspended in the sample chamber and rotatable about an axis, a sealable fluid pressurizing inlet for pressurizing the sample chamber and a pressure gauge for measuring the pressure in the sample chamber when pressurized, and/or a temperature source for heating the solids-laden fluid sample; and a detector that receives the backscattering signal and generates an output signal corresponding to a concentration of solids in the solids-laden fluid sample.

Embodiment A may have one or more of the following additional elements in any combination:

Element A1: Wherein the sample chamber comprises the temperature source and further comprises a plurality of thermal conductivity probes to measure the thermal conductivity of the solids-laden fluid sample.

Element A2: Wherein the sample chamber comprises the temperature source and further comprises a plurality of thermal conductivity probes to measure the thermal conductivity of the solids-laden fluid sample, and wherein the plurality of thermal conductivity probes are evenly distributed along a height or width of the sample chamber.

Element A3: Wherein the sample chamber comprises the sealable fluid pressurizing inlet, the sealable fluid pressurizing inlet connected to a pressurizing fluid source providing pressurizing fluid.

By way of non-limiting example, exemplary combinations applicable to Embodiment A include: A with A1 and A2; A with A1 and A3; A with A2 and A3; A with A1, A2, and A3.

Embodiment B

A method comprising: providing an electromagnetic radiation source that emits electromagnetic radiation; providing a sample chamber comprising a fluid sample inlet for introducing a solids-laden fluid sample therein, the sample chamber further comprising one or more of: a shear bob for applying a shear rate to the solids-laden fluid sample, the shear bob suspended in the sample chamber and rotatable about an axis; a sealable fluid pressurizing inlet for pressurizing the sample chamber and a pressure gauge for measuring the pressure in the sample chamber when pressurized; and/or a temperature source for heating the solids-laden fluid sample; transmitting the electromagnetic radiation from the electromagnetic radiation source and through the sample chamber to optically interact the electromagnetic radiation with the solids-laden fluid and generate a backscattering signal; receiving the backscattering signal with a detector; and generating an output signal corresponding to a concentration of solids in the solids-laden fluid sample.

Embodiment B may have one or more of the following additional elements in any combination:

Element B1: Further comprising determining a solids carrying capacity of the solids-laden fluid sample based on the output signal.

Element B2: Further comprising determining a solids carrying capacity of the solids-laden fluid sample based on the output signal, and further comprising assigning a solids carrying capacity threshold to the solids-laden fluid sample, and wherein the solids-laden fluid sample is reformulated if the output signal exceeds the solids carrying capacity threshold.

Element B3: Wherein the sample chamber comprises the shear bob, and further comprising rotating the shear bob to apply a shear rate to the solids-laden fluid prior to transmitting the electromagnetic radiation through the sample chamber and optically interacting the electromagnetic radiation with the solids-laden fluid.

Element B4: Wherein the sample chamber comprises the shear bob, and further comprising rotating the shear bob to apply a shear rate to the solids-laden fluid prior to transmitting the electromagnetic radiation through the sample chamber and optically interacting the electromagnetic radiation with the solids-laden fluid, and wherein the shear rate applied over time is maintained at a steady state over time, is increased over time, or is decreased over time.

Element B5: Wherein the sample chamber comprises the shear bob, and further comprising rotating the shear bob to apply a shear rate to the solids-laden fluid prior to transmitting the electromagnetic radiation through the sample chamber and optically interacting the electromagnetic radiation with the solids-laden fluid, and further comprising generating a series of output signals corresponding to the concentration of solids in the solids-laden fluid sample over time while applying the shear rate, thereby determining a shear-solids carrying capacity of the solids-laden fluid sample.

Element B6: Wherein the sample chamber comprises the shear bob, and further comprising rotating the shear bob to apply a shear rate to the solids-laden fluid prior to transmitting the electromagnetic radiation through the sample chamber and optically interacting the electromagnetic radiation with the solids-laden fluid, and further comprising generating a series of output signals corresponding to the concentration of solids in the solids-laden fluid sample over time while applying the shear rate, thereby determining a shear-solids carrying capacity of the solids-laden fluid sample, and further comprising assigning a shear-solids carrying capacity threshold to the solids-laden fluid sample, and wherein the solids-laden fluid sample is reformulated if one or more of the series of output signals exceeds the shear-solids carrying capacity threshold.

Element B7: Wherein the sample chamber comprises the sealable fluid pressurizing inlet and a pressure gauge, and further comprising connecting the sealable fluid pressurizing inlet to pressurizing fluid source to pressurize the sample chamber prior to transmitting the electromagnetic radiation through the sample chamber and optically interacting the electromagnetic radiation with the solids-laden fluid.

Element B8: Wherein the sample chamber comprises the sealable fluid pressurizing inlet and a pressure gauge, and further comprising connecting the sealable fluid pressurizing inlet to pressurizing fluid source to pressurize the sample chamber prior to transmitting the electromagnetic radiation through the sample chamber and optically interacting the electromagnetic radiation with the solids-laden fluid, and wherein the pressure in the pressurized sample chamber is maintained at a steady state over time, is increased over time, or is decreased over time.

Element B9: Wherein the sample chamber comprises the sealable fluid pressurizing inlet and a pressure gauge, and further comprising connecting the sealable fluid pressurizing inlet to pressurizing fluid source to pressurize the sample chamber prior to transmitting the electromagnetic radiation through the sample chamber and optically interacting the electromagnetic radiation with the solids-laden fluid, and further comprising generating a series of output signals corresponding to the concentration of solids in the solids-laden fluid sample over time at a pressure corresponding to the pressurized sample chamber reading on the pressure gauge, thereby determining a pressurized-solids carrying capacity of the solids-laden fluid sample.

Element B10: Wherein the sample chamber comprises the sealable fluid pressurizing inlet and a pressure gauge, and further comprising connecting the sealable fluid pressurizing inlet to pressurizing fluid source to pressurize the sample chamber prior to transmitting the electromagnetic radiation through the sample chamber and optically interacting the electromagnetic radiation with the solids-laden fluid, and further comprising generating a series of output signals corresponding to the concentration of solids in the solids-laden fluid sample over time at a pressure corresponding to the pressurized sample chamber reading on the pressure gauge, thereby determining a pressurized-solids carrying capacity of the solids-laden fluid sample, and further comprising assigning a pressurized-solids carrying capacity threshold to the solids-laden fluid sample, and wherein the solids-laden fluid sample is reformulated if one or more of the series of output signals exceeds the pressurized-solids carrying capacity threshold.

Element B11: Wherein the sample chamber comprises the temperature source, and further comprising heating the sample chamber prior to transmitting the electromagnetic radiation through the sample chamber and optically interacting the electromagnetic radiation with the solids-laden fluid.

Element B12: Wherein the sample chamber comprises the temperature source, and further comprising heating the sample chamber prior to transmitting the electromagnetic radiation through the sample chamber and optically interacting the electromagnetic radiation with the solids-laden fluid, and wherein the heat in the sample chamber is maintained at a steady state over time, is increased over time, or is decreased over time.

Element B13: Wherein the sample chamber comprises the temperature source, and further comprising heating the sample chamber prior to transmitting the electromagnetic radiation through the sample chamber and optically interacting the electromagnetic radiation with the solids-laden fluid, and further comprising generating a series of output signals corresponding to the concentration of solids in the solids-laden fluid sample over time, thereby determining a heated-solids carrying capacity of the solids-laden fluid sample.

Element B14: Wherein the sample chamber comprises the temperature source, and further comprising heating the sample chamber prior to transmitting the electromagnetic radiation through the sample chamber and optically interacting the electromagnetic radiation with the solids-laden fluid, and further comprising generating a series of output signals corresponding to the concentration of solids in the solids-laden fluid sample over time, thereby determining a heated-solids carrying capacity of the solids-laden fluid sample, and further comprising assigning a heated-solids carrying capacity threshold to the solids-laden fluid sample, and wherein the solids-laden fluid sample is reformulated if one or more of the series of output signals exceeds the heated-solids carrying capacity threshold.

Element B15: Further comprising a plurality thermal conductivity probes distributed along a height or width of the sample chamber to measure the thermal conductivity of the solids-laden fluid sample in the heated sample chamber, wherein the thermal conductivity is used to determine a concentration of low gravity solids and high gravity solids in the solids-laden fluid sample.

By way of non-limiting example, exemplary combinations applicable to Embodiment B include: B with B1 and B2; B with B1, B2, and B15; B with B2 and B10; B with B3, B4, and B6; B with B8 and B11; B with B2, B5, B9, and B13; B with B13 and B14; B with B8, B9, and B10; B with B4 and B7; B with B3, B6, and B14.

Therefore, the present disclosure is well adapted to attain the ends and advantages mentioned as well as those that are inherent therein. The particular embodiments disclosed above are illustrative only and may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range, is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An apparatus comprising:
an electromagnetic radiation source that emits electromagnetic radiation; a sample chamber comprising a fluid sample inlet for introducing a solids-laden fluid sample therein,
wherein the electromagnetic radiation transmits through the sample chamber and optically interacts with the solids-laden fluid sample to generate a backscattering signal, the sample chamber further comprising one or more of:
a shear bob for applying a shear rate to the solids-laden fluid sample, the shear bob suspended in the sample chamber and rotatable about an axis,
a sealable fluid pressurizing inlet for pressurizing the sample chamber and a pressure gauge for measuring the pressure in the sample chamber when pressurized, and/or
a temperature source for heating the solids-laden fluid sample; and a detector that receives the backscattering signal and generates an output signal corresponding to a concentration of solids in the solids-laden fluid sample a signal processor configured to:
determine a solids carrying capacity of the solids-laden fluid sample based on the output signal: and
assign a solids carrying capacity threshold to the solids-laden fluid sample: and a mixing tank configured to reformulate the solids-laden fluid sample if the output signal exceeds the solids carrying capacity threshold.

2. The apparatus of claim 1, wherein the sample chamber comprises the temperature source and further comprises a plurality of thermal conductivity probes to measure the thermal conductivity of the solids-laden fluid sample.

3. The apparatus of claim 2, wherein the plurality of thermal conductivity probes are evenly distributed along a height or width of the sample chamber.

4. The apparatus of claim 1, wherein the sample chamber comprises the sealable fluid pressurizing inlet, the sealable fluid pressurizing inlet connected to a pressurizing fluid source providing pressurizing fluid.

5. A method comprising:
providing an electromagnetic radiation source that emits electromagnetic radiation;
providing a sample chamber comprising a fluid sample inlet for introducing a solids-laden fluid sample therein, the sample chamber further comprising one or more of:
a shear bob for applying a shear rate to the solids-laden fluid sample, the shear bob suspended in the sample chamber and rotatable about an axis;

a sealable fluid pressurizing inlet for pressurizing the sample chamber and a pressure gauge for measuring the pressure in the sample chamber when pressurized; and/or a temperature source for heating the solids-laden fluid sample;

transmitting the electromagnetic radiation from the electromagnetic radiation source and through the sample chamber to optically interact the electromagnetic radiation with the solids-laden fluid sample and generate a backscattering signal;

receiving the backscattering signal with a detector;

generating an output signal corresponding to a concentration of solids in the solids-laden fluid sample;

determining a solids carrying capacity of the solids-laden fluid sample based on the output signal; and assigning a solids carrying capacity threshold to the solids-laden fluid sample, and wherein the solids-laden fluid sample is reformulated if the output signal exceeds the solids carrying capacity threshold.

6. A method comprising:

providing an electromagnetic radiation source that emits electromagnetic radiation;

providing a sample chamber comprising a fluid sample inlet for introducing a solids-laden fluid sample therein, the sample chamber further comprising one or more of:

a shear bob for applying a shear rate to the solids-laden fluid sample, the shear bob suspended in the sample chamber and rotatable about an axis;

a sealable fluid pressurizing inlet for pressurizing the sample chamber and a pressure gauge for measuring the pressure in the sample chamber when pressurized; and/or a temperature source for heating the solids-laden fluid sample;

transmitting the electromagnetic radiation from the electromagnetic radiation source and through the sample chamber to optically interact the electromagnetic radiation with the solids-laden fluid sample and generate a backscattering signal;

receiving the backscattering signal with a detector;

generating an output signal corresponding to a concentration of solids in the solids-laden fluid sample, wherein the sample chamber comprises the shear bob;

rotating the shear bob to apply a shear rate to the solids-laden fluid sample prior to transmitting the electromagnetic radiation through the sample chamber and optically interacting the electromagnetic radiation with the solids-laden fluid sample; and generating a series of output signals corresponding to the concentration of solids in the solids-laden fluid sample over time while applying the shear rate, thereby determining a shear-solids carrying capacity of the solids-laden fluid sample.

7. The method of claim 6, wherein the shear rate applied over time is maintained at a steady state over time, is increased over time, or is decreased over time.

8. The method of claim 6, further comprising assigning a shear-solids carrying capacity threshold to the solids-laden fluid sample, and wherein the solids-laden fluid sample is reformulated if one or more of the series of output signals exceeds the shear-solids carrying capacity threshold.

9. A method comprising:

providing an electromagnetic radiation source that emits electromagnetic radiation;

providing a sample chamber comprising a fluid sample inlet for introducing a solids-laden fluid sample therein, the sample chamber further comprising one or more of:

a shear bob for applying a shear rate to the solids-laden fluid sample, the shear bob suspended in the sample chamber and rotatable about an axis;

a sealable fluid pressurizing inlet for pressurizing the sample chamber and a pressure gauge for measuring the pressure in the sample chamber when pressurized; and/or a temperature source for heating the solids-laden fluid sample;

transmitting the electromagnetic radiation from the electromagnetic radiation source and through the sample chamber to optically interact the electromagnetic radiation with the solids-laden fluid sample and generate a backscattering signal;

receiving the backscattering signal with a detector;

generating an output signal corresponding to a concentration of solids in the solids-laden fluid sample, wherein the sample chamber comprises the sealable fluid pressurizing inlet and a pressure gauge;

connecting the sealable fluid pressurizing inlet to pressurizing fluid source to pressurize the sample chamber prior to transmitting the electromagnetic radiation through the sample chamber and optically interacting the electromagnetic radiation with the solids-laden fluid sample; and generating a series of output signals corresponding to the concentration of solids in the solids-laden fluid sample over time at a pressure corresponding to a pressurized sample chamber reading on the pressure gauge, thereby determining a pressurized-solids carrying capacity of the solids-laden fluid sample.

10. The method of claim 9, wherein the pressure in the pressurized sample chamber is maintained at a steady state over time, is increased over time, or is decreased over time.

11. The method of claim 9, further comprising assigning a pressurized-solids carrying capacity threshold to the solids-laden fluid sample, and wherein the solids-laden fluid sample is reformulated if one or more of the series of output signals exceeds the pressurized-solids carrying capacity threshold.

12. A method comprising:

providing an electromagnetic radiation source that emits electromagnetic radiation;

providing a sample chamber comprising a fluid sample inlet for introducing a solids-laden fluid sample therein, the sample chamber further comprising one or more of:

a shear bob for applying a shear rate to the solids-laden fluid sample, the shear bob suspended in the sample chamber and rotatable about an axis;

a sealable fluid pressurizing inlet for pressurizing the sample chamber and a pressure gauge for measuring the pressure in the sample chamber when pressurized; and/or a temperature source for heating the solids-laden fluid sample;

transmitting the electromagnetic radiation from the electromagnetic radiation source and through the sample chamber to optically interact the electromagnetic radiation with the solids-laden fluid sample and generate a backscattering signal;

receiving the backscattering signal with a detector;

generating an output signal corresponding to a concentration of solids in the solids-laden fluid sample, wherein the sample chamber comprises the temperature source;

heating the sample chamber prior to transmitting the electromagnetic radiation through the sample chamber and optically interacting the electromagnetic radiation with the solids-laden fluid sample; and generating a series of output signals corresponding to the concentration of solids in the solids-laden fluid sample over time, thereby determining a heated-solids carrying capacity of the solids-laden fluid sample.

13. The method of claim 12, wherein the heat in the sample chamber is maintained at a steady state over time, is increased over time, or is decreased over time.

14. The method of claim 12, further comprising assigning a heated-solids carrying capacity threshold to the solids-laden fluid sample, and wherein the solids-laden fluid sample is reformulated if one or more of the series of output signals exceeds the heated-solids carrying capacity threshold.

15. A method comprising:

providing an electromagnetic radiation source that emits electromagnetic radiation;

providing a sample chamber comprising a fluid sample inlet for introducing a solids-laden fluid sample therein, the sample chamber further comprising one or more of:

a shear bob for applying a shear rate to the solids-laden fluid sample, the shear bob suspended in the sample chamber and rotatable about an axis;

a sealable fluid pressurizing inlet for pressurizing the sample chamber and a pressure gauge for measuring the pressure in the sample chamber when pressurized; and/or a temperature source for heating the solids-laden fluid sample;

transmitting the electromagnetic radiation from the electromagnetic radiation source and through the sample chamber to optically interact the electromagnetic radiation with the solids-laden fluid sample and generate a backscattering signal;

receiving the backscattering signal with a detector;

generating an output signal corresponding to a concentration of solids in the solids-laden fluid sample;

measuring a thermal conductivity of the solids-laden fluid sample in the heated solid-laden fluid sample using a plurality thermal conductivity probes distributed along a height or width of the sample chamber; and determining a concentration of low gravity solids and high gravity solids in the solids-laden fluid sample using the thermal conductivity.

* * * * *